United States Patent [19]

Krebs

[11] Patent Number: 4,685,904
[45] Date of Patent: Aug. 11, 1987

[54] NEEDLE CONSTRUCTION FOR AXILLARY PLEXUS BRACHIALIS ANESTHESIA

[76] Inventor: Peter Krebs, Am Lorettowäldchen 4, 7730 VS-Villingen, BRD, Fed. Rep. of Germany

[21] Appl. No.: 747,666

[22] Filed: Jun. 21, 1985

[30] Foreign Application Priority Data

Jul. 28, 1984 [DE] Fed. Rep. of Germany ....... 3427951
Mar. 7, 1985 [DE] Fed. Rep. of Germany ....... 3508013

[51] Int. Cl.$^4$ ............................................. A61M 5/00
[52] U.S. Cl. .................................... 604/164; 604/239; 604/274; 128/754
[58] Field of Search ............... 604/164, 165, 274, 280, 604/239; 128/754

[56] References Cited

U.S. PATENT DOCUMENTS

| | | | |
|---|---|---|---|
| 3,454,006 | 7/1969 | Langdon | 604/164 |
| 4,191,186 | 3/1980 | Keeler | 604/164 |
| 4,256,119 | 3/1981 | Gauthier | 604/165 X |
| 4,403,617 | 9/1983 | Tretinyak | 604/164 |
| 4,487,209 | 12/1984 | Mehl | 128/754 |
| 4,543,092 | 9/1985 | Mehler et al. | 604/164 |

Primary Examiner—Stephen C. Pellegrino
Attorney, Agent, or Firm—McGlew & Tuttle

[57] ABSTRACT

A combination needle for the axillary plexus brachialis anesthesia comprises a plastic tube and a solid steel mandrel that can be inserted in this plastic tube. The mandrel has a puncturing tip without any facets or cutting edges, which is formed either by a level partially ground surface extending at an angle to the mandrel axis that is elliptical in form and forms a wedge angle of at least 45° with the mandrel axis, or by a right or oblique cone with right or bulging mantle surface and with a cone angle of at least 60°. The handle of the steel mandrel is equipped with partially a ground surface and has, on one side surface, a visible and palpable mark with a fixed angular location corresponding to the angular location of a partially ground surface of the tip, so that it can be used to determine the angular location of the partially ground surface accurately, at all times. Furthermore, a plug-in socket for the electrical connection of an electrostimulator is advantageously provided at the handle of the mandrel.

18 Claims, 13 Drawing Figures

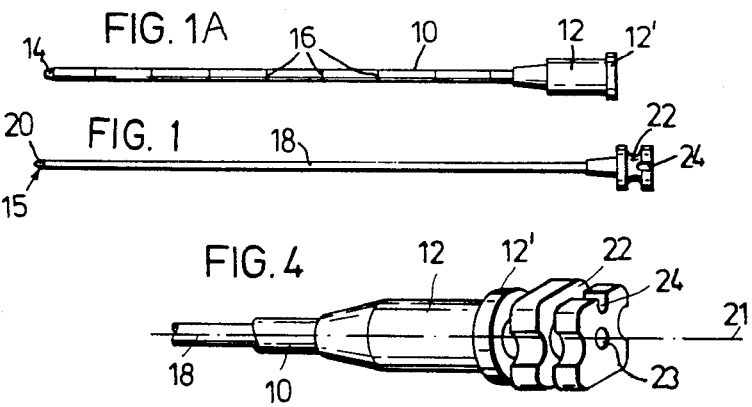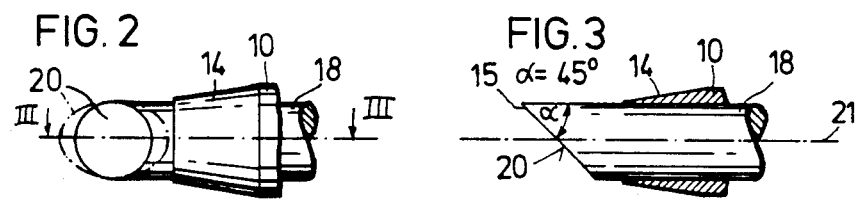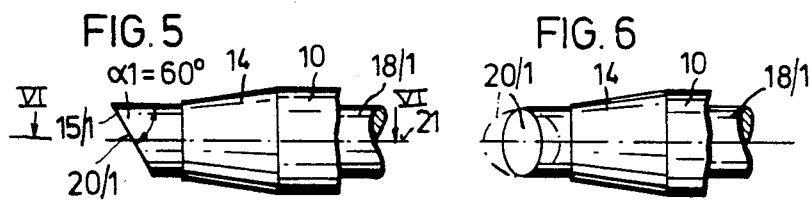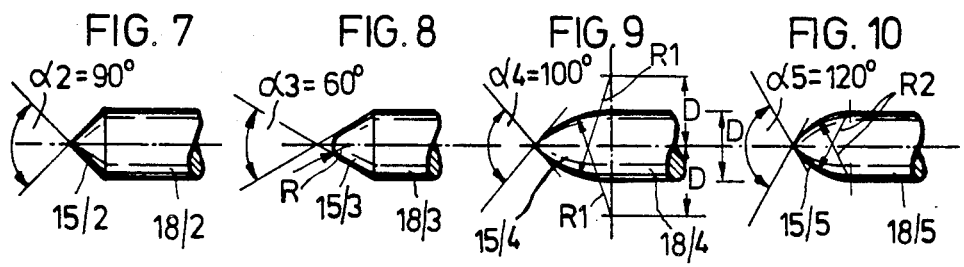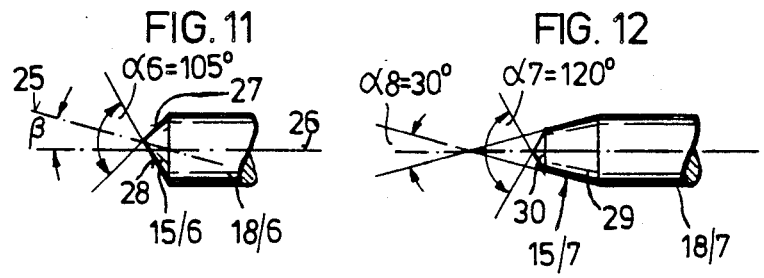

NEEDLE CONSTRUCTION FOR AXILLARY PLEXUS BRACHIALIS ANESTHESIA

FIELD AND BACKGROUND OF THE INVENTION

This invention relates in general to anesthestic devices and in particular a new and useful device for facilitating the puncture of a person's tissue for the purpose of administering an anesthetic.

The invention concerns a combination needle for axillary plexus brachialis anesthesia, consisting of a plastic tube and a cylindrical steel mandrel with a handle and a partially ground puncturing tip, which can be inserted into the plastic tube so that its puncturing tip extends through the front end of the plastic tube.

A plexus brachialis block in the axillary area is preferred for anesthesia and analgesia of the arm. Known for this purpose is a combination needle of this type (Regional-Anasthesia 6: 43–46, 1983). This combination consists of a hollow, i.e. tubular or cannula-like steel mandrel with a sharp tip ground at an angle of less than 45° and equipped with lateral facets (Crawford grinding) as well as a plastic tube of polytetrafluoroethylene, into which the hollow steel mandrel can be inserted in such a way that its ground tip extends through the front end of the plastic tube.

For the puncturing, this combination needle with the hollow, sharp tip extending through the front end of the plastic tube is advanced first until the steel mandrel's tip touches the nerve sheat (neurovascular fascia) of the axillary plexus brachialis nerve. Then, the nerve sheath is punctured with the steel mandrel, and the plastic tube is advanced into the nerve sheath along the steel mandrel. The steel mandrel is then retracted from the plastic tube. An anesthetic can then be injected through the empty plastic tube. The introduction of a thin, flexible catheter through the plastic tube lying in the nerve sheath is also possible.

After puncturing, the resistance of the tissue to the advancing steel mandrel's tip during the advancing of the needle is low up to the nerve sheath. But as soon as the point of the steel mandrel touches the nerve sheath, a perceptibly greater resistance is felt immediately, which decreases instantly, however, at the moment when the nerve sheath is punctured again. This change in resistance to the advancing needle can be used to check the exact location of the needle. This is possible only to a limited extent with the known needle since it has a sharp tip with sharp cutting edges, which strongly reduces the perceptibility of the change in resistance. This is not the only reason for attaching to the shaft, of the steel mandrel of the known combination needle, a syringe with physiological saline solution, to make the resistance to the advancing needle noticeable also as a piston pressure at the syringe. But the syringe attached to the steel mandrel makes the handling of the known needle cumbersome and difficult. The laterally partially ground facets at the hollow tip of the steel mandrel produce a sharp tip, despite the angle of grinding of 45°, which is greater than that of conventional needles, as well as in laterally extending sharp cutting edges that facilitate the puncturing of the nerve sheath but make the danger of damage to nerves and vessels unavoidable. Finally, the laterally ground facets with their cutting edges at the hollow steel mandrel's cause a certain punching or cutting off action during the insertion of the combination needle with the hollow mandrel, which has the consequenc that infected skin components or deeper lying tissue particles can be carried further down and cause infections.

SUMMARY OF THE INVENTION

The invention provides a combination needle for axillary plexus brachialis anesthesia which eliminates at least most of the described danger of damage to nerves and vessels, while being easy to handle, and guarantees a simple and more exact locating of the needle tip especially during its positioning and puncturing of the nerve sheath.

This objective is realized with a steel mandrel that comprises a solid rod which has a puncturing tip without facets and cutting edges, formed by either a level partially ground surface extending at an angle to the mandrel axis and having the shape of an ellipse bound by the mantle area and which forms a notch angle of at least 45° with the mandrel axis, or which is formed by a cone with a right or bulging mantle area and with a cone angle of at least 60°.

In contrast to the known combination needle, the combination needle according to the invention has a solid, rod-shaped, rather than hollow, steel mandrel puncturing tip which has with a level, elliptical partially ground surface without facets and cutting edges forming an angle of at least 45° with the axis, or a conical mantle area with a cone angle of at least 60°, i.e. and is thus relatively blunt. This configuration of the puncturing tip of the solid steel mandrel avoids sharp cutting edges in any event, so that no tissue parts corresponding to the cylindrical shape of a hollow mandrel are dislocated downward with the needle tip when the needle is inserted, which is the case with the known combination needle. In contrast, during the insertion of the solid puncturing tip of the steel mandrel that is relatively blunt according to the invention, the tissue offers a distinctly perceptible puncture resistance, which allows an exact locating of the needle's tip from the outside at all times and without additional aids, as e.g. the attached syringe in the case of the known combination needle. This simplifies the handling of the combination needle considerably, while also greatly improving the aim and the patient's safety. The relatively blunt, solid puncturing tip has the special advantage that the puncturing of the nerve sheath is more clearly perceptible and that the sudden and strong decrease of the resistance to the puncture following the puncturing of the nerve sheath even becomes distinctly audible as a clicking noise.

Beyond the above, the combination needle according to the invention with its variants allows the application of a new method of anesthesia. For examples, with the combination needle according to the invention having the proper length the medication to be applied can be introduced from the axilla directly to the level of the clavicle, where the nerves are more fasciculated. This improves the rate of accuracy of the aim for regional local anesthesia.

The introduction of the combination needle from the axilla reduces the rate of complications considerably in comparison with the insertion above the clavicle.

Experience shows that the different configurations of the puncturing tip of the steel mandrel can be selected for optimal effect in various cases of application, e.g. according to age or sex.

The handle part of the steel mandrel that has a puncturing tip with unilateral partially ground surfaces or slanted cone shapes bears a visible or palpable mark, e.g. in the form of a groove, a notch or a rib that is located in the axial plane of symmetry of the ground surface and is thus immovably coordinated with the angular position of the partially ground surface or the oblique cone tip. This is a simple means of indicating at all times the position of the partially ground surface or the cone tip, e.g. with resepct to the axillary artery.

The handle of the steel mandrel with a unilateral ground surface or an oblique cone tip has an at least approximately square shape in a known manner when seen axially from above, which permits a turning of the steel mandrel about its longitudinal axis for the positioning of the ground surface or the oblique cone tip with respect to the axillary artery in a more sensitive manner.

Since the handle of the solid steel mandrel is equipped with an electrical plug-in socket, the possiblity of connecting an electrical nerve stimulator for the determination of the position of the steel mandrel tip by means of a nerve stimulation via the mandrel point is given. Since the plastic tube provides electrical insulation for the steel mandrel, the electro-stimulation is produced in the form of a point at the puncturing tip of the steel mandrel extending beyond the plastic tube, which allows a very exact determination of the location.

After the perforation of the vasometer nerve sheath by the puncturing tip of the steel mandrel, the plastic tube is advanced in a known manner on the steel mandrel and brought into the desired position where it is to remain. The steel mandrel is then retracted from the plastic tube. The exactly positioned plastic tube can then be used for the injection of an anesthetic or as guiding tube for a flexible catheter that is to be inserted.

Accordingly it is an object of the invention to provide an anesthetic needle construction which includes an outer sheath and a mandrel in the sheath which has a tip with a ground surface disposed at an angle of at least 45°.

A further object of the invention is to provide a combination needle and plastic tube which includes a mandrel in the plastic tube which projects from an open end of the tube and has a puncturing tip which is formed in the shape of an ellipse bound by a surface which forms a wedge angle of at least 45° which is formed by a cone with a bulging mantle surface and has a cone angle of at least 60°.

A further object of the invention is to provide a mandrel for the administering of an anesthetic which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1 is a side elevational view of a combination needle according to the invention, showing the steel mandrel constructed according to the invention;

FIG. 1A is a similar view of a plastic tube, with the steel mandrel retracted from the plastic tube and shown separately;

FIG. 2 is an enlarged diagram of the tip of the assembled combination needle in a side view showing a unilateral, slanted partially ground surface;

FIG. 3 is a section taken along the line III—III of FIG. 2;

FIG. 4 is an enlarged perspective of the back handle end of the combination needle;

FIG. 5 is a view similar to FIG. 2, but with a different partially ground surface of the puncturing tip of the steel mandrel;

FIG. 6 is a section taken along the line VI—VI of FIG. 5;

FIGS. 7 to 12 are end elevational views of various conical puncturing tips fitting steel mandrels with the same diameter, enlarged.

DESCRIPTION OF THE PREFERRED EMBODIMENTS

Referring to the drawings in particular, the invention as embodied therein in in FIGS. 1A, 1 and 4 comprises a mandrel for administering an anesthetic which includes a mandrel 18 which is insertable through a plastic tube 10 so that its puncturing tip 15 projects beyond the open end or tip 14 of the tube 10. In accordance with the invention the mandrel has a puncturing tip without facets and cutting edges that includes a ground surface which extends at an angle to the axis of the mandrel of at least 45°. This surface may either be a single wedge shaped surface or a conical formation and the location of the puncturing tip may be determined at all times by the position of an indicator 24 on a handle portion 22 which projects out the end of a shaft portion 12 of the plastic tube 10 and may be manipulated accurately.

The combination needle comprises a plastic tube 10 made of polytetrafluoroethylene, which has at its back end a shaft 12 having a larger diameter and a flanged ring 12′, as well as of a solid cylindrical steel mandrel 18. Tip 14 of the plastic tube 10 is conically tapered. A scale of lengths in centimeters is arranged in the form of circular markings 16 on the mantle surface of plastic tube 10.

It is expedient to produce the plastic tube in two sizes. For use for the high axillary plexus anesthesia, the plastic tube has a diameter of 1.6 mm and a length of 8.3 cm. For use of the regular axillary plexus anesthesia, the tube has a diameter of 1.3 mm and a length of 5.1 cm.

The solid steel mandrel 18 intended for insertion into plastic tube 10 can be advanced through shaft 12 into plastic tube 10 to a point where its puncturing tip 15 extends from the plastic tube tip 14. The steel mandrel 18 is thus longer than plastic tube 10 by at least the axial length of its oblique puncturing tip 15.

The practical example shown in FIG. 2 and 3 has a steel mandrel 18 that is unilaterally partially ground at its tip 15 in such a way that a partially ground surface 20 forms a wedge-shaped angle $\alpha$ of 45° with axis 21. This partially ground surface 20 has the geometric form of an ellipse formed exclusively by the cylindrical mantle surface of steel mandrel 18 and is completely devoid of facets. This partial grinding of puncturing tip 15 of steel mandrel 18 avoids sharp cutting edges. But a puncturing tip is formed that possesses adequate puncturing characteristics even for the piercing of the relatively resistant vasomotor nerve sheath and at the same time makes the initially mentioned change in entering resistance readily audible.

In the practical example of the solid steel mandrel 18/1 shown in FIGS. 5 and 6, the wedge angle $\alpha$ 1 of the unilateral partially ground surface 20/1 is 60°. The puncturing tip 15/1 formed by it is therefore blunter than the puncturing tip of FIGS. 2 and 3.

In FIGS. 2 and 6, side views of the partially ground surfaces 20 and 20/1, respectively, extending perpendicular to the axis 21, are represented by solid lines. Their elliptical forms, indicated by dots and dashes, are apparent when the partially ground surfaces 20 and 20/1 are viewed vertically from above. The puncturing tip 15/2 of the solid steel mandrel of FIG. 7 consists of a straight, pointed cone with a cone angle α 2 of 90°.

The cone angle α 3 of the also cone-shaped puncturing tip 15/3 of solid steel mandrel 18/3 in FIG. 8 is only 60°; but the cone tip is rounded in the form of a spherical segment, and the radius R of the spherical segment corresponds to approximately one-half of diameter D of steel mandrel 18/3.

In FIGS. 9 and 10, the puncturing tips 15/4 and 15/5 of steel mandrel 18/4 and 18/5, respectively, are shaped as bulging cones with different radii of curvature R1 and R2. The radius of curvature R1 for the more slender puncturing tip 15/4 of steel mandrel corresponds to 1.5 times the diameter D, which results in a cone angle α 4 of approximately 100° at the tip.

The radius of curvature R2 of the blunder puncturing tip 15/5 corresponds exactly to diamter D, resulting in a cone angle α 5 of approximatley 120° at the tip.

The puncturing tip 15/6 of steel mandrel 18/6 shown in FIG. 11 is formed by an oblique cone, and its axis of symmetry 25 forms an angle β of 15° with the axis of the mandrel, while its cone angle α 6 is approximately 105°. Depending on whether its short mantle surface side 27 or the long mantle surface side 28 is placed at the vasomotor nerve sheath (neurovascular fascia) to be perforated, the dissymmetry provides this puncturing tip 15/6 with different puncturing characteristics that allow the person handling it a very sensitive and optimal manipulation, for example by placing the blunt, i.e. longer mantle surface side 28 of the cone angle against the sheath and then gradually turning steel mandrel 18/6 toward the short pointed mantle surface side 27, while maintaining a steady puncturing pressure.

Finally, FIG. 12 shows a steel mandrel 18/7 with a two-phase cone shaped puncturing tip 15/7, which consists of a more slender section 29 with a cone angle α 8 of 30° and a blunt bottom part 30 with a cone angle α 7 of 120°.

It is obvious that different shapes that are within the range of similarity may be chosen for the puncturing tip of the solid steel mandrel, which may have other cone angles α and/or another angle of obliqueness β, for example. Important in each case is the absence of sharp cutting edges, which prevents the cutting off of tissue particles during puncturing or penetrating tissue and the good locating of puncturing tip 15 to 15/7 at all times.

Steel mandrel 18 has a handle 22 at the bottom end, which serves as stop during the insertion of steel mandrel 18 into plastic tube 10 and limits the depth of insertion. This handle 22 has a generally square shape when seen axially from above. Handle 22 has in one of its side surfaces a mark 24 in the form of a notch or an axial groove, which could also have the shape of an axial rib or similar configuration. The angular position of this mark 24 corresponds to the angular position of the partially ground surfaces 20 and 20/1 on the steel mandrels 18 and 18/1, i.e. mark 24 lies exactly in the axial plane of symmetry of partially ground surface 20, so that this mark 24 can be used to feel or read at any time the angular position of partially ground surface 20 or 20/1 at the notch. Such a mark 24 is also used to advantage for steel mandrel 18/6 with puncturing tip 15/5 consisting of an oblique cone, when it is located preferably in the plane at handle 22 in which the two axes 25 and 26 are lying.

The face at the back of handle 22 contains a plug-in socket 23 located coaxially with axis 21 of the steel mandrel. This plug-in socket 23 can receive the electrical plug type connection of an electro-stimulator. The plug-in socket 23 may contain a spring to hold an inserted miniature connection reliably by clamping action. As is clear from FIGS. 1, 1A and 4, socket 23 is sized relative to large diameter shaft 12 such that the internal diameter of socket 23 is relatively smaller than that of said shaft 12.

While specific embodiments of the invention have been shown and described in detail to illustrate the application of the principles of the invention, it will be understood that the invention may be embodied otherwise without departing from such principles.

What is claimed is:

1. Combination needle for axillary plexus brachialis anesthesia comprising a plastic tube having an open front end and an open rear end, said rear end being formed as a relatively large diameter hollow shaft portion having a given internal diameter, and a cylindrical steel mandrel having a handle adjacent one end and a partially ground puncturing tip adjacent its opposite end and which is inserted in said plastic tube so that its handle acts as a stop against said hollow shaft portion and its puncturing tip extends through said open front end a selective distance in relation to the stop acting positioning of said handle against said hollow shaft portion, said mandrel comprising a solid cylindrical puncturing tip of generally blunt end shape, which is without facets and cutting edges, and which includes a ground surface extending at an apex angle of at least 45° at the tip of the mandrel, and said handle having a plug-in socket for clamping action holding of a relatively miniature electrical connection of an electro-stimulator, said socket having an internal diameter which is relatively smaller than the corresponding internal diameter of said larger diameter hollow shaft portion.

2. Needle of claim 1, wherein said handle has a handle portion with an outer surface having a palpable mark located in the axial plane of said ground surface of the puncturing tip.

3. Needle of claim 2, wherein said handle is substantially rectangular.

4. Needle of claim 1, wherein said plastic tube comprises flexible material having a scale of lengths on its exterior surface.

5. Needle of claim 1, wherein said plastic tube has a diameter of 1.6 mm and a length of 83 mm.

6. Needle of claim 1, wherein said plastic tube has a diameter of 1.3 mm and a length of 51 mm.

7. Needle of claim 1, wherein said mandrel comprises a solid part having a puncturing tip without facets and cutting edges, and which is formed by a partially ground surface extending at an angle to the mandrel axis that has the blunt end shape of an ellipse forming a mantle surface and which forms a wedge angle of at least 45° with the axis of said mandrel.

8. Needle of claim 1, wherein said mandrel comprises a solid part having a puncturing tip without facets and cutting edges, and which is formed by a cone with a blunt end shape forming a mantle surface and which forms a cone angle of at least 60°.

9. Needle of claim 8, wherein the cone forms a right cone mantle surface.

10. Needle of claim 8, wherein the cone forms a bulging cone mantle surface.

11. Needle of claim 1, wherein said puncturing tip is of solid steel having a cone angle of less than 90° and is rounded in a shape of a spherical segment.

12. Needle of claim 11, wherein the radius of curvature of the rounded part of the puncturing tip corresponds substantially to one-quarter of the diameter of said mandrel.

13. Needle of claim 1, wherein said ground surface comprises a cone having a bulging mantle surface with a radius of convexity of substantially the diameter of said mandrel.

14. Needle of claim 1, wherein said ground surface comprises a cone having a bulging mantle surface with a radius of convexity maximally greater by one-half than the diameter of said mandrel.

15. Needle of claim 1, wherein said ground surface comprises an oblique cone approximately one-half the diameter of said mandrel with a cone angle of at least 90° and having a slender truncated cone with an acute angle which is not more than 40° connected to said oblique cone.

16. Needle of claim 1, wherein said puncturing tip has a shape of an oblique cone with a cone axis which is inclined at a angle of approximately 15° to 20° with respect to the mandrel axis.

17. Needle of claim 16 wherein the angle of the cone is approximately 100° to 120°.

18. Combination needle for axillary plexis brachialis anesthesia comprising a plastic tube having an open front end, and a cylindrical steel mandrel having a handle adjacent one end and a partially ground puncturing tip adjacent its opposite end and which is inserted in said plastic tube so that its puncturing tip extends through said open front end, said mandrel comprising a solid cylindrical puncturing tip of generally blunt end shape, which is without facets and cutting edges, and which includes a ground surface having the blunt end shape of an ellipse forming a wedge angle of at least 45 degrees to the axis of the mandrel.

* * * * *